(12) United States Patent
Freier

(10) Patent No.: US 6,750,019 B2
(45) Date of Patent: Jun. 15, 2004

(54) ANTISENSE MODULATION OF INSULIN-LIKE GROWTH FACTOR BINDING PROTEIN 5 EXPRESSION

(75) Inventor: Susan M. Freier, San Diego, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/975,123

(22) Filed: Oct. 9, 2001

(65) Prior Publication Data

US 2003/0087857 A1 May 8, 2003

(51) Int. Cl.$^7$ ............... C12Q 1/68; C12P 19/34; C12N 15/88; C07H 21/02; C07H 21/04
(52) U.S. Cl. ............... 435/6; 435/91.1; 435/458; 536/23.1; 536/24.5
(58) Field of Search ............... 435/6, 91.1, 91.31, 435/325, 375, 455, 458; 536/23.1, 23.2, 24.3, 24.31, 24.33, 24.5; 514/44

(56) References Cited

U.S. PATENT DOCUMENTS 5,877,309 A * 3/1999 McKay et al. ............... 536/24.5

FOREIGN PATENT DOCUMENTS

| EP | WO 01/05435 | * | 7/2000 |
|---|---|---|---|
| WO | WO 92/03470 | | 3/1992 |
| WO | WO 92/03471 | | 3/1992 |
| WO | WO 01/05435 | | 1/2001 |

OTHER PUBLICATIONS

Giorgio Pald et al. Journal of Biotechnology 68 (1999) pp. 1–13.*
Andrea D. Branch. TIBS 23—Feb. 1998. pp. 45–50.*
Ingo Tamm et al., The Lancet, vol. 358. Aug. 11, 2001, pp. 489–497.*
Karen Pihl–Carey The Daily Biotechnology Newspaper, vol. 10. No. 239. pp. 1–2.*
Stanley T. Crooke, pp. 1–50.*
Sudhir Agrawal et al., Molecular Medicine Today, Feb. 2000, vol. 6, pp. 72–81.*
Hideaki Miyake et al., International Journal of Urology (2001) 8 pp. 337–349.*
Mariarosa A B Melone et al. Journal of Cellular Physiology, 185, pp. 143–153. (2000).*
Allander et al., *Characterization of the chromosomal gene and promoter for human insulin–like growth factor binding protein–5*, J. Biol. Chem., 1994, 269:10891–10898.
Huynh et al., *A role for insulin–like growth factor binding protein 5 in the antiproliferative action of the antiestrogen ICI 182780*, Cell Growth Differ., 1996, 7:1501–1506.
James et al., *Insulin–like growth factor binding protein–5 modulates muscle differentiation through an insulin–like growth factor–dependent mechanism*, J. Cell Biol., 1996, 133:683–693.
Kou et al., *Identification of two clusters of mouse insulin–like growth factor binding protein genes on chromosomes 1 and 11*, Genomics, 1994, 21:653–655.

Melone et al., *Increased expression of IGF–binding protein–5 in Duchenne muscular dystrophy (DMD) fibroblasts correlates with the fibroblast–induced downregulation of DMD myoblast growth: an in vitro analysis*, J. Cell Physiol., 2000, 185:143–153.
Miyake et al., *Castration–induced up–regulation of insulin–like growth factor binding protein–5 potentiates insulin–like growth factor–I activity and accelerates progression to androgen independence in prostate cancer models*, Cancer Res., 2000, 60:3058–3064.
Miyakoski et al., *Evidence that IGF binding protein–5 functions as a growth factor*, J. Clin. Invest., 2001, 137:73–81.
Parisot et al., *Induction of insulin–like growth factor binding protein expression by ICI 182, 780 in a tamoxifen–resistant human breast cancer cell line*, Breast Cancer Res. Treat., 1999, 55:231–242.
Rozen et al., *Inhibition of insulin–like growth factor I receptor signaling by the vitamin D analogue EB1089 in MCF T breast cancer cells: A role for insulin like*.
Shamasaki et al., *Identification of five different insulin–like growth factor binding proteins (IGFBPs) from adult rat serum and molecular cloning of a novel IGFBP–5 in rat and human*, J. Biol. Chem., 1991, 266:10646–10653.
Twigg et al., *Insulin–like growth factor (IGF)—binding protein 5 forms an alternative ternary complex with IGFs and the acid–labile subunit*, J. Biol. Chem., 1998, 273:6074–6079.
Twigg et al., *Insulin–like growth factor–binding protein 5 complexes with the acid–labile subunit. Role of the carboxyl–terminal domain*, J. Biol.Chem., 1998, 273:28791–28798.
Van Kleffens et al., *Generation of antisera to mouse insulin–like growth factor binding proteins (IGFBP)—1 to –6: comparison of IGFBP protein and messenger ribonucleic acid localization in the mouse embryo*, Endocrinology, 1999, 140:5944–5952.
Wetterau et al., *Novel aspects of the insulin–like growth factor binding proteins*, Mol. Genet. Metab., 1999, 68:161–181.
Wulbrand et al., *mRNA expression patterns of insulin–like growth factor system components in human neuroendocrine tumours*, Eur. J. Clin. Invest., 2000, 30:729–739.
Beeh et al., *Differential expression and localization of IGF–I and IGF binding proteins in inflamed rat colon*, J. Recept. Signal Transduct. Res., 1998, 18:265–289.

* cited by examiner

Primary Examiner—Ram R. Shukla
Assistant Examiner—Jane Zara
(74) Attorney, Agent, or Firm—Licata & Tyrrell P.C.

(57) ABSTRACT

Antisense compounds, compositions and methods are provided for modulating the expression of insulin-like growth factor binding protein 5. The compositions comprise antisense compounds, particularly antisense oligonucleotides, targeted to nucleic acids encoding insulin-like growth factor binding protein 5. Methods of using these compounds for modulation of insulin-like growth factor binding protein 5 expression and for treatment of diseases associated with expression of insulin-like growth factor binding protein 5 are provided.

13 Claims, No Drawings

ANTISENSE MODULATION OF INSULIN-LIKE GROWTH FACTOR BINDING PROTEIN 5 EXPRESSION

FIELD OF THE INVENTION

The present invention provides compositions and methods for modulating the expression of insulin-like growth factor binding protein 5. In particular, this invention relates to compounds, particularly oligonucleotides, specifically hybridizable with nucleic acids encoding insulin-like growth factor binding protein 5. Such compounds have been shown to modulate the expression of insulin-like growth factor binding protein 5.

BACKGROUND OF THE INVENTION

The insulin-like growth factor (IGF) family includes insulin-like growth factors type I and II (IGF-I and IGF-II) which are structurally related to pro-insulin. IGFs act as potent mitogens to regulate somatic growth, cellular proliferation, and cellular differentiation. Their action is determined by the availability of free IGFs to interact with IGF receptors. The level of free IGFs in a cell is modulated by the rate of IGF production and clearance, and also by their interaction with insulin-like growth factor binding proteins (IGFBPs) and IGFBP-related proteins (IGFBP-rPs) (Wetterau et al., *Mol. Genet. Metab.*, 1999, 68, 161–181).

The superfamily of insulin-like growth factor binding proteins comprises six IGFBPs that bind to IGFs with high affinity, and an emerging group of nine IGFBP-related proteins which bind to IGFs with lower affinity. Cleavage of IGFBPs by proteases also modulates the levels and the action of free IGFs and IGFBPs. IGFBPs not only regulate IGF action and bioavailability, but also appear to mediate IGF-independent actions including inhibition or enhancement of cell growth and induction of apoptosis. The growth inhibitory effects of sequestration by IGFBPs are evidenced when they competitively bind IGFs and modulate their interactions with type I IGF cell surface receptors (Wetterau et al., *Mol. Genet. Metab.*, 1999, 68, 161–181).

Using the amino terminal sequence of the purified rat insulin-like growth factor binding protein 5 (also known as insulin-like growth factor binding protein 5 precursor, IGF-binding protein 5, IGFBP5, igfbp-5, and IBP5) to prepare degenerate oligonucleotide probes, the rat and human genes were cloned from rat ovary and human placental cDNA libraries (Shimasaki et al., *J. Biol. Chem.*, 1991, 266, 10646–10653). The human genes for insulin-like growth factor binding protein 5 and insulin-like growth factor binding protein 2 are physically linked, as are the homologous mouse genes, which colocalize on mouse chromosome 1 in a region of synteny with the human chromosomal locus 2q33-q36 (Kou et al., *Genomics*, 1994, 21, 653–655). The human gene was mapped to chromosome 2 using a panel of somatic cell hybrids, and by fluorescence in situ hybridization to the 2q33-q34 locus (Allander et al., *J. Biol. Chem.*, 1994, 269, 10891–10898).

Disclosed and claimed in the PCT publications WO 92/03470 and WO 92/03471 are recombinant DNA molecules encoding insulin-like growth factor binding protein 5 and subsequences thereof, microorganisms and cell lines containing said molecules, methods for preparing insulin-like growth factor binding protein 5 from these, and the purified protein itself, as well as antibodies to the protein and derivatives thereof (Kiefer and Masiarz, 1992; Kiefer et al., 1992).

Fetal tissues express high levels of insulin-like growth factor binding protein 5 during rapid growth, but tissue levels vary in adults. Insulin-like growth factor binding protein 5 is the main IGFBP expressed in the kidney and it is found in substantial amounts in connective tissues and cerebrospinal fluid. Serum levels of insulin-like growth factor binding protein 5 also decrease with age, starting after puberty. Levels in older women are 30% of those of teenagers (Wetterau et al., *Mol. Genet. Metab.*, 1999, 68, 161–181).

Insulin-like growth factor binding protein 5 has several unique features that suggest it is a key component of the IGF system in bone. Bone cells produce large amounts of insulin-like growth factor binding protein 5, but levels decrease during maturation due to protease activity. Unlike other IGFBPs, insulin-like growth factor binding protein 5 has a high specific binding affinity for hydroxyapatite and extracellular matrix proteins, and thus it is stored in abundance within bone. It appears to act as a growth factor, stimulating bone formation via a mechanism independent of IGF-I, an effect specific for insulin-like growth factor binding protein 5 and not other IGFBPs. It is the only IGFBP shown to stimulate osteoblast cell proliferation in vitro. A single local injection of insulin-like growth factor binding protein 5 into the outer periosteum of the parietal bone of IGF-I knockout mice increased alkaline phosphatase and osteocalcin levels of calvarial bone extracts. A significant age-related decrease in insulin-like growth factor binding protein 5 could contribute in part to the age-related impairment in the coupling of bone formation to resorption (Miyakoshi et al., *J. Clin. Invest.*, 2001, 107, 73–81).

Insulin-like growth factor binding protein 5 is a component of a ternary complex in human serum. The other two components of this complex are an insulin-like growth factor and a glycoprotein known as the acid labile subunit (ALS). Formation of this ternary complex stabilizes insulin-like growth factor binding protein 5 levels and is hypothesized to provide a circulating reservoir of insulin-like growth factor binding protein 5 and IGFs, implying a previously unrecognized form of IGF transport and delivery in the circulation and a novel mechanism for regulating its bioavailability (Twigg and Baxter, *J. Biol. Chem.*, 1998, 273, 6074–6079). A basic carboxyl-terminal domain of the protein is the principal site in insulin-like growth factor binding protein 5 responsible for ALS binding (Twigg et al., *J. Biol. Chem.*, 1998, 273, 28791–28798).

Specific antisera against insulin-like growth factor binding protein 5 have been generated. Mouse embryos as well as tissues from mice with a targeted disruption of insulin-like growth factor binding protein 5 were used to confirm histochemically that insulin-like growth factor binding protein 5 is expressed in various tissues such as kidney, liver, endothelium of the gut, tubules and mesenchyme of the lung, meninges, notochord, muscle and tongue. Differences between mRNA and protein localization suggest that the protein is secreted and transported (van Kleffens et al., *Endocrinology*, 1999, 140, 5944–5952).

Levels of insulin-like growth factor binding protein 5 mRNA are increased in inflamed colon smooth muscle cells in an experimental model of colitis in rat (Zeeh et al., *J. Recept. Signal Transduct. Res.*, 1998, 18, 265–280).

Insulin-like growth factor binding protein 5 has also been implicated in prostate cancer progression (Miyake et al., *Cancer Res.*, 2000, 60, 3058–3064), is expressed with high frequency in neuroendocrine tumors (Wulbrand et al., *Eur. J. Clin. Invest.*, 2000, 30, 729–739), and has been shown to be induced upon treatment of breast cancer cells with antiestrogens used to abolish tamoxifen resistant proliferation (Huynh et al., *Cell Growth Differ.*, 1996, 7, 1501–1506; Parisot et al., Breast Cancer Res. Treat., 1999, 55, 231–242).

The pharmacological modulation of insulin-like growth factor binding protein 5 activity and/or expression is therefore believed to be an appropriate point of therapeutic intervention in developmental or growth disorders, and in pathological conditions such as cancer, colitis, Duchenne muscular dystrophy, diabetes and other metabolic diseases, such as osteoporosis and osteopetrosis.

Antisense mediated inhibition of insulin-like growth factor binding protein 5 has been utilized as an investigative tool to elucidate its mitogenic action in IGF signal transduction pathways and as a therapeutic agent for prostate cancer progression in a mouse model (Miyake et al., *Cancer Res.*, 2000, 60, 3058–3064).

A phosphorothioate antisense oligonucleotide, 18 nucleotides in length and complementary to the translation initiation site of the mouse insulin-like growth factor binding protein 5 mRNA, was used to inhibit its expression and show that the mouse insulin-like growth factor binding protein 5, which is up-regulated after castration, potentiates IGF-I activity and accelerates progression to androgen independence. Mice bearing androgen-dependent Shionogi prostate tumors were temporally delayed in their progression to androgen independence and recurrence of androgen independent tumors was inhibited when this antisense oligonucleotide was administered systemically (Miyake et al., *Cancer Res.*, 2000, 60, 3058–3064).

Approximately 1.2 kilobase pairs of the insulin-like growth factor binding protein 5 cDNA was cloned in the antisense orientation with respect to the Moloney sarcoma virus promoter in an expression vector. This construct was used to produce antisense sequences complementary to the mRNA for investigation of the role of insulin-like growth factor binding protein 5 in autocrine secretion by C2 myoblasts. Myoblasts expressing the insulin-like growth factor binding protein 5 antisense transcript differentiate prematurely and more extensively than control cells, consistent with a model in which insulin-like growth factor binding protein 5 blocks IGF-stimulated myogenesis. A possible mechanism of action involves sequestration of IGFs in the extracellular matrix (James et al., *J. Cell Biol.*, 1996, 133, 683–693).

A phosphorothioate antisense oligonucleotide, 15 nucleotides in length and complementary to a region of the mRNA encompassing the start codon, was used to inhibit expression of insulin-like growth factor binding protein 5 and show that insulin-like growth factor binding protein 5 acts as a diffusible factor to sequester IGFs and/or other growth factors to downregulate Duchenne muscular dystrophy (DMD) myoblast proliferation (Melone et al., *J. Cell Physiol.*, 2000, 185, 143–153).

A phosphorothioate antisense oligonucleotide, 21 nucleotides in length and complementary to nucleotides 813–834 of Genbank Accession NM_000599, has been used in two studies to inhibit the expression of insulin-like growth factor binding protein 5. In the first study, expression of insulin-like growth factor binding protein 5 is induced by the antiestrogen ICI 182780 and that insulin-like growth factor binding protein 5 assists the drug in inhibiting proliferation of MCF-7 breast cancer cells (Huynh et al., *Cell Growth Differ.*, 1996, 7, 1501–1506). The same antisense oligonucleotide was later used to demonstrate that the effect of a vitamin D analogue EB1089, which also inhibits proliferation and induce apoptosis of MCF-7 breast carcinoma cells, is attenuated when insulin-like growth factor binding protein 5 is not expressed (Rozen and Pollak, *Int. J. Oncol.*, 1999, 15, 589–594).

Disclosed and claimed in PCT Publication WO 01/05435 is a method for treating hormone-regulated tumors (for example breast and prostatic tumors) in mammals including humans, by administration of antisense oligonucleotides. The antisense oligonucleotides disclosed are designed to target the murine and human insulin-like growth factor binding protein 5 genes (Gleave, 2001).

Currently, there are no known therapeutic agents which effectively inhibit the synthesis of human insulin-like growth factor binding protein 5. Consequently, there remains a long felt need for additional agents capable of effectively inhibiting insulin-like growth factor binding protein 5 function.

Antisense technology is emerging as an effective means for reducing the expression of specific gene products and may therefore prove to be uniquely useful in a number of therapeutic, diagnostic, and research applications for the modulation of insulin-like growth factor binding protein 5 expression.

The present invention provides compositions and methods for modulating insulin-like growth factor binding protein 5 expression.

SUMMARY OF THE INVENTION

The present invention is directed to compounds, particularly antisense oligonucleotides, which are targeted to a nucleic acid encoding insulin-like growth factor binding protein 5, and which modulate the expression of insulin-like growth factor binding protein 5. Pharmaceutical and other compositions comprising the compounds of the invention are also provided. Further provided are methods of modulating the expression of insulin-like growth factor binding protein 5 in cells or tissues comprising contacting said cells or tissues with one or more of the antisense compounds or compositions of the invention. Further provided are methods of treating an animal, particularly a human, suspected of having or being prone to a disease or condition associated with expression of insulin-like growth factor binding protein 5 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding insulin-like growth factor binding protein 5, ultimately modulating the amount of insulin-like growth factor binding protein 5 produced. This is accomplished by providing antisense compounds which specifically hybridize with one or more nucleic acids encoding insulin-like growth factor binding protein 5. As used herein, the terms "target nucleic acid" and "nucleic acid encoding insulin-like growth factor binding protein 5" encompass DNA encoding insulin-like growth factor binding protein 5, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of insulin-like growth factor binding protein 5. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding insulin-like growth factor binding protein 5. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding insulin-like growth factor binding protein 5, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA) In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$-)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, (filed Oct. 23, 1992) the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al.,*Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol Exp. Ther.,* 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of insulin-like growth factor binding protein 5 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding insulin-like growth factor binding protein 5, enabling sandwich and other assays to easily be constructed to exploit this fact. Hybridization of the antisense oligonucleotides of the invention with a nucleic acid encoding insulin-like growth factor binding protein 5 can be detected by means known in the art. Such means may include conjugation of an enzyme to the oligonucleotide, radiolabelling of the oligonucleotide or any other suitable detection means. Kits using such detection means for detecting the level of insulin-like growth factor binding protein 5 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_1$–$C_{10}$ alkyl ester (e.g. isopropylmyristate IPM), monoglyceride, diglyceride or pharmaceutically acceptable salt thereof. Topical formulations are described in detail in U.S. patent application Ser. No. 09/315,298 (filed on May 20, 1999) which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/ salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. Nos. 08/886,829 (filed Jul. 1, 1997), 09/108,673 (filed Jul. 1, 1998), 09/256, 515 (filed Feb. 23, 1999), 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 $\mu$m in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms,* Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms,* Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms,* Lieberman, Rieger and Banker (Eds.), 1988, Marcel Dekker, Inc., New York, N.Y., volume 1, p. 335; Idson, in *Pharmaceutical Dosage Forms,* Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms,* Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms,* Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms,* Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems,* Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences,* Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms,* Lieberman, Rieger and Banker (Eds.), 1988, Marcel Dekker, Inc., New York, N.Y., volume 1, p. 245; Block, in *Pharmaceutical Dosage Forms,* Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research,* 1994, 11, 1385–1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research,* 1994, 11, 1385; Ho et al., *J. Pharm. Sci.,* 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms,* Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S. T. P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside GM1 or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are selfoptimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms,* Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms,* Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.,* 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p.92; Muranishi, *Critical Reviews in Therapeutic Drug Carrier Systems,* 1990, 7, 1–33; El Hariri et al., *J. Pharm. Pharmacol.,* 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 *In: Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis
Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro Amidites
2'-Fluorodeoxyadenosine Amidites

2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-o-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane (4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 h the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_3)_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl Uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2
Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry,* 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Insulin-Like Growth Factor Binding Protein 5 Expression Antisense modulation of insulin-like growth factor binding protein 5 expression can be assayed in a variety of ways known in the art. For example, insulin-like growth factor binding protein 5 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of insulin-like growth factor binding protein 5 can be quantitated in a variety of ways well known in the art, such as immunoprecipitation, Western blot analysis (immunoblotting), ELISA or fluorescence-activated cell sorting (FACS). Antibodies directed to insulin-like growth factor binding protein 5 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13
Real-Time Quantitative PCR Analysis of Insulin-Like Growth Factor Binding Protein 5 mRNA Levels Quantitation of insulin-like growth factor binding protein 5 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 μL PCR cocktail (1×TAQMAN™ buffer A, 5.5 mM MgCl$_2$, 300 μM each of dATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human insulin-like growth factor binding protein 5 were designed to hybridize to a human insulin-like growth factor binding protein 5 sequence, using published sequence information (GenBank accession number M65062, incorporated herein as SEQ ID NO:3). For human insulin-like growth factor binding protein 5 the PCR primers were:

forward primer: CCAAACACACCCGCATCTC (SEQ ID NO: 4)
reverse primer: TTGGACTGGGTCAGCTTCTTTC (SEQ ID NO: 5) and the PCR probe was: FAM-AGGCTGAAGCAGTGAAGAAGGACCGC-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

forward primer: GAAGGTGAAGGTCGGAGTC (SEQ ID NO: 7)
reverse primer: GAAGATGGTGATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of Insulin-Like Growth Factor Binding Protein 5 mRNA Levels Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human insulin-like growth factor binding protein 5, a human insulin-like growth factor binding protein 5 specific probe was prepared by PCR using the forward primer CCAAACACACCCGCATCTC (SEQ ID NO: 4) and the reverse primer TTGGACTGGGTCAGCTTCTTTC (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human Insulin-Like Growth Factor Binding Protein 5 Expression by Chimeric Phosphorothioate Oligonucleotides Having 2'-MOE Wings and a Deoxy Gap In accordance with the present invention, a series of oligonucleotides were designed to target different regions of the human insulin-like growth factor binding protein 5 RNA, using published sequences (GenBank accession number M65062, incorporated herein as SEQ ID NO: 3, GenBank accession number NM_000599, incorporated herein as SEQ ID NO: 10, residues 135001–156000 of Genbank accession number AC007563, incorporated herein as SEQ ID NO: 11, and GenBank accession number AF147308, incorporated herein as SEQ ID NO: 12). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human insulin-like growth factor binding protein 5 mRNA levels by quantitative real-time PCR as described in other examples herein. Data are averages from two experiments. If present, "N.D." indicates "no data".

TABLE 1

Inhibition of human insulin-like growth factor binding protein 5 mRNA levels by chimeric phosphorothioate oligonucleotides have 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 154897 | Start Codon | 3 | 36 | gagcaacaccatcttctctt | 87 | 13 |
| 154898 | Coding | 3 | 65 | taggcggccagcagcaggag | 72 | 14 |
| 154899 | Coding | 3 | 299 | gcgtgcagcggcttctcctc | 69 | 15 |
| 154900 | Coding | 3 | 306 | cagcagggcgtgcagcggct | 78 | 16 |
| 154901 | Coding | 3 | 333 | ttcgttgaggcaaacccgc | 50 | 17 |
| 154902 | Coding | 3 | 338 | ctctttcgttgaggcaaac | 67 | 18 |
| 154903 | Coding | 3 | 342 | gtagctcttttcgttgaggc | 87 | 19 |
| 154904 | Coding | 3 | 497 | tttctgcggtccttcttcac | 12 | 20 |
| 154905 | Coding | 3 | 503 | agcttctttctgcggtcctt | 90 | 21 |
| 154906 | Coding | 3 | 511 | actgggtcagcttctttctg | 43 | 22 |
| 154907 | Coding | 3 | 518 | aacttggactgggtcagctt | 79 | 23 |
| 154908 | Coding | 3 | 580 | cctgtctcatctcaggtgca | 62 | 24 |
| 154909 | Coding | 3 | 651 | catgcgtgggctggctttga | 78 | 25 |
| 154910 | Coding | 3 | 656 | ggcaccatgcgtgggctggc | 76 | 26 |
| 154911 | Coding | 3 | 676 | tgggcaggtacacagcacgg | 82 | 27 |
| 154912 | Coding | 3 | 698 | tagaatcctttgcggtcaca | 72 | 28 |
| 154913 | Coding | 3 | 703 | tcttgtagaatcctttgcgg | 56 | 29 |
| 154914 | Coding | 3 | 709 | gctttctcttgtagaatcct | 57 | 30 |
| 154915 | 3' UTR | 3 | 986 | gtcctcagtttcctcaaata | 74 | 31 |
| 154916 | 3' UTR | 3 | 991 | ccgaggtcctcagtttcctc | 89 | 32 |
| 154917 | 3' UTR | 3 | 996 | agattccgaggtcctcagtt | 87 | 33 |
| 154918 | 3' UTR | 3 | 1001 | gctagagattccgaggtcct | 89 | 34 |
| 154919 | 3' UTR | 3 | 1006 | cccttgctagagattccgag | 94 | 35 |
| 154920 | 3' UTR | 3 | 1186 | cctaactctattcgtcttc | 61 | 36 |
| 154921 | 3' UTR | 3 | 1394 | ggagaggtcctggagtgttt | 0 | 37 |
| 154922 | 3' UTR | 3 | 1579 | gatctgcttccgaaaacctc | 86 | 38 |
| 154923 | 5' UTR | 10 | 11 | ctttgcagctctttcctagc | 80 | 39 |
| 154924 | 5' UTR | 10 | 584 | cttgcaaaaatgtagagaga | 73 | 40 |
| 154925 | Intron 1 | 11 | 4214 | gctttggctgcctgccacct | 79 | 41 |

TABLE 1-continued

Inhibition of human insulin-like growth factor binding
protein 5 mRNA levels by chimeric phosphorothioate
oligonucleotides have 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 154926 | Intron 1: Exon 2 | 11 | 16817 | ctgcaggagaaggagccgga | 72 | 42 |
| 154927 | 3' UTR | 12 | 197 | actgtagtcaccgtggaaga | 88 | 43 |

As shown in Table 1, SEQ ID NOs 13, 14, 15, 16, 17, 18, 19, 21, 23, 24, 25, 26, 27, 28, 29, 30, 31, 32, 33, 34, 35, 36, 38, 39, 40, 41, 42 and 43 demonstrated at least 50% inhibition of human insulin-like growth factor binding protein 5 expression in this assay and are therefore preferred. The target sites to which these preferred sequences are complementary are herein referred to as "active sites" and are therefore preferred sites for targeting by compounds of the present invention.

Example 16
Western Blot Analysis of Insulin-Like Growth Factor Binding Protein 5 Protein Levels Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to insulin-like growth factor binding protein 5 is used, with a radio-labelled or fluorescently labeled secondary antibody directed against the primary antibody species. Bands are visualized using a PHOSPHORIMAGER™ (Molecular Dynamics, Sunnyvale Calif.).

What is claimed is:

1. An antisense oligonucleotide 8 to 50 nucleobases in length targeted to nucleobases 580 through 599 nucleobases or nucleobases 676 through 728 of a coding region, nucleobases 996 through 1205 or nucleobases 1579 through 1598 of a 3' untranslated region of a nucleic acid molecule (SEQ ID NO: 3) encoding insulin-like growth factor binding protein 5, nucleobases 11 through 30 or nucleobases 584 through 603 of a nucleic acid molecule (SEQ ID NO: 10) encoding insulin-like growth factor binding protein 5, nucleobases 4214 through 4233 of an intron region or nucleobases 16817 through 16836 of an intron/exon junction region of a nucleic acid molecule (SEQ ID NO: 11) encoding insulin-like growth factor binding protein 5, or nucleobases 197 through 216 of a 3' untranslated region of a nucleic acid molecule (SEQ ID NO: 12) encoding insulin-like growth factor binding protein 5, wherein said oligonuclectide specifically hybridizes with one of said regions and inhibits the expression of insulin-like growth factor binding protein 5.

2. The antisense oligonucleotide of claim 1 wherein the antisense oligonucleotide has a sequence comprising SEQ ID No: 15, 18, 23, 24, 26, 27, 28, 29, 30, 33, 34, 35, 36, 38, 39, 40, 41, 42 or 43.

3. The antisense oligonucleotide of claim 1 wherein the antisense oligonucleotide comprises at least one modified internucleoside linkage.

4. The antisense oligonucleotide of claim 3 wherein the modified initernucleoside linkage is a phosphorothioate linkage.

5. The antisense oligonucleotide of claim 1 wherein the antisense oligonucleotide comprises at least one modified sugar moiety.

6. The antisense oligonucleotide of claim 5 wherein the modified sugar moiety is a 2'-o-methoxyethyl sugar moiety.

7. The antisense oligonucleotide of claim 1 wherein the antisense oligonucleotide comprises at least one modified nucleobase.

8. The antisense oligonucleotide of claim 7 wherein the modified nucleobase is a 5-methylcytosine.

9. The antisense oligonucleotide of claim 1 wherein the antisense oligonucleotide is a chimeric oligonucleotide.

10. A composition comprising the antisense oligonucleotide of claim 1 and a pharmaceutically acceptable carrier or diluent.

11. The composition of claim 10 further comprising a colloidal dispersion system.

12. A method of inhibiting the expression of insulin-like growth factor binding protein 5 in cells or tissues in vitro comprising contacting said cells or tissues in vitro with the antisense oligonucleotide of claim 1 so that expression of insulin-like growth factor binding protein 5 is inhibited.

13. An antisense oligonucleotide consisting of SEQ ID NO: 14, 16, 17, 19, 21 or 25.

* * * * *

UNITED STATES PATENT AND TRADEMARK OFFICE
CERTIFICATE OF CORRECTION

PATENT NO. : 6,750,019 B2
DATED : June 15, 2004
INVENTOR(S) : Susan M. Freier

It is certified that error appears in the above-identified patent and that said Letters Patent is hereby corrected as shown below:

Title page,
Item [56], References Cited, OTHER PUBLICATIONS,
"Giorgio" reference, delete "Pald" and insert -- Palu' --;
"Miyakoski" reference, delete "Miyakoski" and insert -- Miyakoshi --;
"Rozen" reference, delete "MCF T" and insert -- MCF-7 --;
"Shamasaki" reference, delete "Shamasaki" and insert -- Shimasaki --;
"Beeh" reference, delete "Beeh" and insert -- Zeeh --;

Column 83,
Line 37, delete the second occurrence of "nucleobases";
Lines 52-53, delete "oligonuclectide" and insert -- oligonucleotide --.

Signed and Sealed this

Third Day of January, 2006

JON W. DUDAS
*Director of the United States Patent and Trademark Office*

SEQUENCE LISTING

```
<160> NUMBER OF SEQ ID NOS: 43

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                              20

<210> SEQ ID NO 3
<211> LENGTH: 1612
<212> TYPE: DNA
<213> ORGANISM: Homo sapiens
<220> FEATURE:
<221> NAME/KEY: CDS
<222> LOCATION: (44)...(862)

<400> SEQUENCE: 3
ctctcctgcc ccaccccgag gtaaaggggg cgactaagag aag atg gtg ttg ctc      55
                                              Met Val Leu Leu
                                                1 acc gcg gtc ctc ctg ctg ctg gcc gcc tat gcg ggg ccg gcc cag agc     103
Thr Ala Val Leu Leu Leu Leu Ala Ala Tyr Ala Gly Pro Ala Gln Ser
```

-continued

| | 5 | | | 10 | | | 15 | | | 20 | | |
|---|---|---|---|---|---|---|---|---|---|---|---|---|
| ctg | ggc | tcc | ttc | gtg | cac | tgc | gag | ccc | tgc | gac | gag | aaa | gcc | ctc | tcc | 151 |
| Leu | Gly | Ser | Phe | Val | His | Cys | Glu | Pro | Cys | Asp | Glu | Lys | Ala | Leu | Ser | |
| | | | | 25 | | | | 30 | | | | 35 | | | | |

```
ctg ggc tcc ttc gtg cac tgc gag ccc tgc gac gag aaa gcc ctc tcc       151
Leu Gly Ser Phe Val His Cys Glu Pro Cys Asp Glu Lys Ala Leu Ser
                25                  30                  35 atg tgc ccc ccc agc ccc ctg ggc tgc gag ctg gtc aag gag ccg ggc       199
Met Cys Pro Pro Ser Pro Leu Gly Cys Glu Leu Val Lys Glu Pro Gly
                40                  45                  50 tgc ggc tgc tgc atg acc tgc gcc ctg gcc gag ggg cag tcg tgc ggc       247
Cys Gly Cys Cys Met Thr Cys Ala Leu Ala Glu Gly Gln Ser Cys Gly
            55                  60                  65 gtc tac acc gag cgc tgc gcc cag ggg ctg cgc tgc ctc ccc cgg cag       295
Val Tyr Thr Glu Arg Cys Ala Gln Gly Leu Arg Cys Leu Pro Arg Gln
        70                  75                  80 gac gag gag aag ccg ctg cac gcc ctg ctg cac ggc cgc ggg gtt tgc       343
Asp Glu Glu Lys Pro Leu His Ala Leu Leu His Gly Arg Gly Val Cys
85                  90                  95                 100 ctc aac gaa aag agc tac cgc gag caa gtc aag atc gag aga gac tcc       391
Leu Asn Glu Lys Ser Tyr Arg Glu Gln Val Lys Ile Glu Arg Asp Ser
                105                 110                 115 cgt gag cac gag gag ccc acc acc tct gag atg gcc gag gag acc tac       439
Arg Glu His Glu Glu Pro Thr Thr Ser Glu Met Ala Glu Glu Thr Tyr
            120                 125                 130 tcc ccc aag atc ttc cgg ccc aaa cac acc cgc atc tcc gag ctg aag       487
Ser Pro Lys Ile Phe Arg Pro Lys His Thr Arg Ile Ser Glu Leu Lys
        135                 140                 145 gct gaa gca gtg aag aag gac cgc aga aag aag ctg acc cag tcc aag       535
Ala Glu Ala Val Lys Lys Asp Arg Arg Lys Lys Leu Thr Gln Ser Lys
    150                 155                 160 ttt gtc ggg gga gcc gag aac act gcc cac ccc cgg atc atc tct gca       583
Phe Val Gly Gly Ala Glu Asn Thr Ala His Pro Arg Ile Ile Ser Ala
165                 170                 175                 180 cct gag atg aga cag gag tct gag cag ggc ccc tgc cgc aga cac atg       631
Pro Glu Met Arg Gln Glu Ser Glu Gln Gly Pro Cys Arg Arg His Met
                185                 190                 195 gag gct tcc ctg cag gag ctc aaa gcc agc cca cgc atg gtg ccc cgt       679
Glu Ala Ser Leu Gln Glu Leu Lys Ala Ser Pro Arg Met Val Pro Arg
            200                 205                 210 gct gtg tac ctg ccc aat tgt gac cgc aaa gga ttc tac aag aga aag       727
Ala Val Tyr Leu Pro Asn Cys Asp Arg Lys Gly Phe Tyr Lys Arg Lys
        215                 220                 225 cag tgc aaa cct tcc cgt ggc cgc aag cgt ggc atc tgc tgg tgc gtg       775
Gln Cys Lys Pro Ser Arg Gly Arg Lys Arg Gly Ile Cys Trp Cys Val
    230                 235                 240 gac aag tac ggg atg aag ctg cca ggc atg gag tac gtt gac ggg gac       823
Asp Lys Tyr Gly Met Lys Leu Pro Gly Met Glu Tyr Val Asp Gly Asp
245                 250                 255                 260 ttt cag tgc cac acc ttc gac agc agc aac gtt gag tga tgcgtccccc       872
Phe Gln Cys His Thr Phe Asp Ser Ser Asn Val Glu
                265                 270 cccaacctt  ccctcacccc  ctcccacccc  cagccccgac  tccagccagc  gcctccctcc    932
accccaggac  gccactcatt  tcatctcatt  taagggaaaa  atatatatct  atctatttga    992
ggaaactgag  gacctcggaa  tctctagcaa  gggctcaact  tcgaaaatgg  caacaacaga   1052
gatgcaaaaa  gctaaaaaga  caccccccccc  ctttaaatgg  ttttcttttt  gaggcaagtt   1112
ggatgaacag  agaagggaag  agaggaagaa  cgagaggaag  agaagggaag  gaagtgtttg   1172
tgtagaagag  agagaaagac  gaatagagtt  aggaaaagga  agacaagcag  gtgggcagga   1232
aggacatgca  ccgagaccag  gcaggggccc  aactttcacg  tccagccctg  gcctggggtc   1292
```

```
gggagaggtg ggcgctagaa gatgcagccc aggatgtggc aatcaatgac actattgggg    1352
tttcccagga tggattggtc agggggagaa aggaaaaggc aaaacactcc aggacctctc    1412
ccggatctgt ctcctcctct agccagcagt atggacagct ggaccnctga acttcctctc    1472
```
(Note: verifying line 1472: `ccggatctgt ctcctcctct agccagcagt atggacagct ggaccnctga acttcctctc`)

-continued

<223> OTHER INFORMATION: PCR Probe

<400> SEQUENCE: 9
caagcttccc gttctcagcc                                                     20

<210> SEQ ID NO 10
<211> LENGTH: 1722
<212> TYPE: DNA
<213> ORGANISM: Homo sapiens
<220> FEATURE:
<221> NAME/KEY: CDS
<222> LOCATION: (752)...(1570)

<400> SEQUENCE: 10

| | |
|---|---|
| gggaaaaga gctaggaaag agctgcaaag cagtgtgggc tttttcccctt tttttgctcc | 60 |
| ttttcattac ccctcctccg ttttcaccct tctccggact tcgcgtagaa cctgcgaatt | 120 |
| tcgaagagga ggtggcaaag tgggagaaaa gaggtgttag ggtttggggt ttttttgttt | 180 |
| ttgtttttgt tttttaattt cttgatttca acatttctc ccaccctctc ggctgcagcc | 240 |
| aacgcctctt acctgttctg cggcgccgcg caccgctggc agctgagggt tagaaagcgg | 300 |
| ggtgtatttt agattttaag caaaaatttt aaagataaat ccatttttct ctcccacccc | 360 |
| caacgccatc tccactgcat ccgatctcat tatttcggtg gttgcttggg ggtgaacaat | 420 |
| tttgtggctt ttttcccct ataattctga cccgctcagg cttgagggtt tctccggcct | 480 |
| ccgctcactg cgtgcacctg gcgctgccct gcttccccca acctgttgca aggctttaat | 540 |
| tcttgcaact gggacctgct cgcaggcacc ccagccctcc acctctctct acattttgc | 600 |
| aagtgtctgg gggagggcac ctgctctacc tgccagaaat tttaaaacaa aaacaaaaac | 660 |
| aaaaaaatct ccgggggccc tcttggcccc tttatccctg cactctcgct ctcctgcccc | 720 |
| accccgaggt aaaggggcg actaagagaa g atg gtg ttg ctc acc gcg gtc | 772 |
| | Met Val Leu Leu Thr Ala Val |
| | 1         5 |
| ctc ctg ctg gcc gcc tat gcg ggg ccg gcc cag agc ctg ggc tcc | 820 |
| Leu Leu Leu Leu Ala Ala Tyr Ala Gly Pro Ala Gln Ser Leu Gly Ser |
|     10                  15                  20 |
| ttc gtg cac tgc gag ccc tgc gac gag aaa gcc ctc tcc atg tgc ccc | 868 |
| Phe Val His Cys Glu Pro Cys Asp Glu Lys Ala Leu Ser Met Cys Pro |
|         25                  30                  35 |
| ccc agc ccc ctg ggc tgc gag ctg gtc aag gag ccg ggc tgc ggc tgc | 916 |
| Pro Ser Pro Leu Gly Cys Glu Leu Val Lys Glu Pro Gly Cys Gly Cys |
| 40                  45                  50                  55 |
| tgc atg acc tgc gcc ctg gcc gag ggg cag tcg tgc ggc gtc tac acc | 964 |
| Cys Met Thr Cys Ala Leu Ala Glu Gly Gln Ser Cys Gly Val Tyr Thr |
|             60                  65                  70 |
| gag cgc tgc gcc cag ggg ctg cgc tgc ctc ccc cgg cag gac gag gag | 1012 |
| Glu Arg Cys Ala Gln Gly Leu Arg Cys Leu Pro Arg Gln Asp Glu Glu |
|                 75                  80                  85 |
| aag ccg ctg cac gcc ctg ctg cac ggc cgc ggg gtt tgc ctc aac gaa | 1060 |
| Lys Pro Leu His Ala Leu Leu His Gly Arg Gly Val Cys Leu Asn Glu |
|             90                  95                  100 |
| aag agc tac cgc gag caa gtc aag atc gag aga gac tcc cgt gag cac | 1108 |
| Lys Ser Tyr Arg Glu Gln Val Lys Ile Glu Arg Asp Ser Arg Glu His |
|         105                 110                 115 |
| gag gag ccc acc acc tct gag atg gcc gag gag acc tac tcc ccc aag | 1156 |
| Glu Glu Pro Thr Thr Ser Glu Met Ala Glu Glu Thr Tyr Ser Pro Lys |
| 120                 125                 130                 135 |
| atc ttc cgg ccc aaa cac acc cgc atc tcc gag ctg aag gct gaa gca | 1204 |
| Ile Phe Arg Pro Lys His Thr Arg Ile Ser Glu Leu Lys Ala Glu Ala | |

|     |     |     |     |     |     |     |     |     |     |     |     |     |     |      |
| --- | --- | --- | --- | --- | --- | --- | --- | --- | --- | --- | --- | --- | --- | ---- |
|     |     | 140 |     |     |     | 145 |     |     |     | 150 |     |     |     |      |
| gtg | aag | aag | gac | cgc | aga | aag | aag | ctg | acc | cag | tcc | aag | ttt | gtc | ggg | 1252 |
| Val | Lys | Lys | Asp | Arg | Arg | Lys | Lys | Leu | Thr | Gln | Ser | Lys | Phe | Val | Gly |
|     |     | 155 |     |     |     | 160 |     |     |     | 165 |     |     |     |      |
| gga | gcc | gag | aac | act | gcc | cac | ccc | cgg | atc | atc | tct | gca | cct | gag | atg | 1300 |
| Gly | Ala | Glu | Asn | Thr | Ala | His | Pro | Arg | Ile | Ile | Ser | Ala | Pro | Glu | Met |
|     | 170 |     |     |     | 175 |     |     |     | 180 |     |     |     |      |
| aga | cag | gag | tct | gag | cag | ggc | ccc | tgc | cgc | aga | cac | atg | gag | gct | tcc | 1348 |
| Arg | Gln | Glu | Ser | Glu | Gln | Gly | Pro | Cys | Arg | Arg | His | Met | Glu | Ala | Ser |
|     | 185 |     |     |     | 190 |     |     |     | 195 |     |     |     |      |
| ctg | cag | gag | ctc | aaa | gcc | agc | cca | cgc | atg | gtg | ccc | cgt | gct | gtg | tac | 1396 |
| Leu | Gln | Glu | Leu | Lys | Ala | Ser | Pro | Arg | Met | Val | Pro | Arg | Ala | Val | Tyr |
| 200 |     |     |     | 205 |     |     |     | 210 |     |     |     | 215 |      |
| ctg | ccc | aat | tgt | gac | cgc | aaa | gga | ttc | tac | aag | aga | aag | cag | tgc | aaa | 1444 |
| Leu | Pro | Asn | Cys | Asp | Arg | Lys | Gly | Phe | Tyr | Lys | Arg | Lys | Gln | Cys | Lys |
|     |     | 220 |     |     |     | 225 |     |     |     | 230 |     |     |     |      |
| cct | tcc | cgt | ggc | cgc | aag | cgt | ggc | atc | tgc | tgg | tgc | gtg | gac | aag | tac | 1492 |
| Pro | Ser | Arg | Gly | Arg | Lys | Arg | Gly | Ile | Cys | Trp | Cys | Val | Asp | Lys | Tyr |
|     |     | 235 |     |     |     | 240 |     |     |     | 245 |     |     |     |      |
| ggg | atg | aag | ctg | cca | ggc | atg | gag | tac | gtt | gac | ggg | gac | ttt | cag | tgc | 1540 |
| Gly | Met | Lys | Leu | Pro | Gly | Met | Glu | Tyr | Val | Asp | Gly | Asp | Phe | Gln | Cys |
|     |     | 250 |     |     |     | 255 |     |     |     | 260 |     |     |     |      |
| cac | acc | ttc | gac | agc | agc | aac | gtt | gag | tga | tgcgtccccc cccaaccttt |     |     |     |     | 1590 |
| His | Thr | Phe | Asp | Ser | Ser | Asn | Val | Glu |     |     |     |     |      |
| 265 |     |     |     |     | 270 |     |     |     |     |     |     |     |      |

```
ccctcacccc ctcccacccc cagccccgac tccagccagc gcctcctcc accccaggac      1650 gccactcatt tcatctcatt taagggaaaa atatatatct atctatttga ggaaaaaaaa      1710
aaaaaaaaaa aa                                                         1722

<210> SEQ ID NO 11
<211> LENGTH: 21000
<212> TYPE: DNA
<213> ORGANISM: Homo sapiens
<220> FEATURE:

<400> SEQUENCE: 11
ggagggaagg ggagacgaag ttactctcct cattgtgttc accctgctcc gaagaactct       60
gtcttccact ggcccctcca cctcctcccc attctcggta gccccagcct gtccccttg      120 ccccttcctt acattccggg gggaggaggg cgctgttcag aggggaggag ggcgctgttc      180
agggagcgaa ggggagcccc cttgtgtcta gaaggcctct ccccaccccc accccgtgtg      240
agtttgtact gcaaagctcc ttggcatcct tgcctgagtt gggtgttggg aagctcaaat      300
tgcagctaca aactggctgg cagccagggg ccggctattt aaaagcgcct gctctcccgg      360
agccccgtag tctctttgga aacttctgca ggggaaaaga gctaggaaag agctgcaaag      420
cagtgtgggc ttttccctt ttttgctcct tttcattacc cctcctccgt tttcacccctt      480 ctccggactt cgcgtagaac ctgcgaattt cgaagaggag gtggcaaagt gggagaaaag      540
aggtgttagg gtttggggtt tttttgtttt tgttttgtt tttaatttc ttgatttcaa       600 cattttctcc caccctctcg gctgcagcca acgcctctta cctgttctgc ggcgccgcgc      660
accgctggca gctgagggtt agaaagcggg gtgtatttta gattttaagc aaaaatttta      720
aagataaatc cattttctc tcccaccccc aacgccatct ccactgcatc cgatctcatt      780
atttcggtgg ttgcttgggg gtgaacaatt ttgtggcttt ttttccccta taattctgac      840
ccgctcaggc ttgagggttt ctccggcctc cgctcactgc gtgcacctgg cgctgccctg      900
```

-continued

```
cttcccccaa cctgttgcaa ggctttaatt cttgcaactg ggacctgctc gcaggcaccc      960
cagccctcca cctctctcta cattttttgca agtgtctggg ggagggcacc tgctctacct   1020
gccagaaatt ttaaaacaaa aacaaaaaca aaaaatctc cggggggccct cttggcccct    1080 ttatccctgc actctcgctc tcctgcccca ccccgaggta aggggggcga ctaagagaag    1140
atggtgttgc tcaccgcggt cctcctgctg ctggccgcct atgcggggcc ggcccagagc    1200
ctgggctcct tcgtgcactg cgagccctgc gacgagaaag ccctctccat gtgcccccc     1260 agccccctgg gctgcgagct ggtcaaggag ccgggctgcg gctgctgcat gacctgcgcc    1320
ctggccgagg ggcagtcgtg cggcgtctac accgagcgct gcgcccaggg gctgcgctgc    1380
ctcccccggc aggacgagga gaagccgctg cacgccctgc tgcacggccg cggggttgc     1440 ctcaacgaaa agagctaccg cgagcaagtc aagatcggtg agcgcgctca gtgtgccagt    1500
cagttacgcg gcgcacgggc gggggacacg agaccggctg ggcccgcgcg ctttgcgcag    1560
caagtggctt cgagctgggg tgcagctcgg gagtagtcgg ggagggtcct tgcaccccgg    1620
aattggagcc ctgaggatc ctgctacccg ggggaactgt ctagccgagt ctatcccagc     1680
tttcgctctt tctccttcct cctacccaca cgttgcccgc cccctcccc tactctgtcc     1740 gaatactgat tctgagctct tattcggtca caaggtccaa atccctggt accctatcta     1800 cagtctgaaa gagtgtatgt tacattatca actccctcct ccaccccct cgcgccccgc     1860 ataggttttt ttctgaactt ggaaaaaaaa tctcttttgt taaaatatta ttttaattgc    1920
ggcctggaga gagaggcatt acctatcttc tgagctaatt ccacctttgt ccctcttggc    1980
ccctccaccc ccgtgcctcc agacgtttct atccctccac ccctacacac acaccacaaa    2040
caccccacat ccttggtagc taatgccttt cgggtgggag ccctgaagcc cctcccatgt    2100
gcataaccat tgcttttttat tgaagatgat tgcctgtggt agatggtaaa acatatttaa    2160
ctgcaaaatg acttttattt tatcccagga agggaaaaaa atactttagg agtgcggggg    2220 tgcgggtgg gggtgggaa gagtagaaag gaagggtttg gtattctgtg cctggtgttc     2280
gtttctgaat ctaattcctt ttcccctct ccaattcaga ttttacctag gatgaaaggt      2340
ggacataggg ctgggaggca aaagggggatg tgagattcag agctttcaac ttcctcgcct   2400
atgcagattc ctggcaccac caccacctcc acccccgccc cgcaattcct ccctccgcaa    2460 tcccccacc ccgccctccc caatctctta aaccagatca caagtgggtg tggattaagt     2520
gcatgagggg ccctggaaac gcagaatgca aaattcaggg ggcggagaca gaaaagccac    2580
gcactgggag cctcgcctcc gcttgccccg ccccgggtt gcgccgcccc caaattctcg     2640
gcgccaggag tctaggggttg aaatgattga cacagctact tgttcaatca gaacagttct   2700
acccccttag actgagtttc tttttggaaa gagttacctg atctttagtt aaaaaaaaaa    2760
aaagttaaat aaaactacata aaagtctggg ttctaagacg tcaaactggc tattgattct   2820
ctccaaaagg ggttaaaact tggctaaaca atgtttattt ggcgtagttt agttacggag    2880
acagtttagt tacggggggca atccccttct ccctcctgt cccttccgt tactcacgag     2940 caccctaaca tgagttttct gaagtgcaaa tttcagtcac tatagtgcag agaggagtg     3000 cgtccgcgct tgccaggagg ccggagagct tcctgtgttc agcctcagtc cccgcaaacc    3060
ctgcagggtt tgagtggcgc aggggccagc ccctctagct ttgcaagagg tagtcgatct    3120
ccaaacctgc aaaagtcga tctttttgca ggttgcagcc tgcaaaaaga ggaaaagggg    3180
aggatgtgca ggctctggga accccagaga ccggcttgtg agattatttt tattaagatc    3240
cacttttcaa aggcggtcct gcccgccttc atcttggggg atgtggattt ggaaaagcct    3300
```

```
agcggagaag gaaaacatta attgatttcc cggcttggga gccaccgccc tgggtaacaa    3360
tccagtcaca ccgaaagaac gtaaggtgtc actcagccgc atcctggctc cacttattat    3420
ttaccaagcg tgtagtgtga tgtggctagt gtgaaggggtg tacacgcaga gcgcacgcgc   3480
gcgcaattgc taggcgagca cggagggcgc atcacacaca cacacacaca cacacacaca    3540
cacacacaca cacgacactt cagtcccaag caagatcccc tgtagaattc cctgccgccc    3600
cttgctcaac ccccaccttc tgagtgcctt tgggccaacc cgaagccgcc tcttctaccc    3660 gcccctccc cagcactcct ctccgactcc accccgccga aggcaggtgc ccggccggct     3720
gctgttgcgg gttggcggcg ctccaccgct gctggtgccg acatcttctt cccgaacaga    3780
tgggatggga gtgggcgctc ctggaaaggg cgttttagcc ggacaaccac tgggcgggtc    3840
cccaaaaagt tggagatggt gtagagaccg ttcttaagga gagagaaatg gacagagaga    3900
gggagagtgc ccttttggtc ctttagccaa aattcctgct tcccaacaca cctcctacct    3960
ccctcctctc ccccaccccc gccaaaatct gagcttgcag atatggattt gcccctccc    4020 tcccgcagtt gcagcataca cacacacaca cacacacaca cacacacaca cacacacacg    4080
acatattata tctatataat tatatattgt atatatggta tatactatat tatatatatt    4140
tatatgtaac caaacatgta gaacccaaaa aaggtgcatt tctggaatca gaaatgggga    4200
gcagaagaga gtgaggtggc aggcagccaa agcctctggg agggaaagga gagggcggag    4260
gagagggtgt tttgctaggc tgttgctgag caactggaga gggagtgggc ccgagagcag    4320
ggtgctgaga gcgagcctgg ctctgcattt cattctggcc agttcaggag cagagataga    4380
tacggaaaaa agaatgtgtg tgaggctgga gggagatgaa agacgggagt tatttgatgg    4440
gcaaagctca gtaaatagcg gtgagtggag ggagtcaagg aagtactggg tttgctttcg    4500
ggcatttttg gtggggaatg aggtttgatg ggctggtccc cagcatagat accggggttc    4560
gggtaggtct cctctgtgct ggtgagacat tcagtttaag atgtagggag ccgtgggttc    4620
tggctttcgg ttctgtcatt aagaaatgag acaccgtggg acaaaaaata ggcttctgga    4680
aaagaaagca aaagcattac ctaaatattaaaa gtgaattcag cctttgcttc tttgaggggt    4740
ttggcctcca tcaccctggc ttcaactcca agcctggtct aaaatgccat gttgaagtcg    4800
agttccagag ttaggtttat tggccaaatt tatgtctggg ttgagcaaga tcatggaaaa    4860
ctgaaggagc caaattcctt tcccacccgc acccccctccc tctgaaacaa gtctttgaga   4920
ggatggcgtg ccctgagcca accaaaacgg gagttgggaa aacgagatgg ggctttaact    4980
ggacttttct cgccacctcc gcccaccgcc ccgcccccg cccacccgc cccccctccc     5040 ccacctttct gctgtgtcag ctcagactgg aagaacaagc agagttagcc ctagtgagag    5100
ctcatattct ttccatttct cttttttcccc tttctcaccc ctccctccta ctcttccctc   5160
cgaccttctc catccaccc ccgacccccc accccaactc taaggcatcc cctgagggct     5220
tgagttttaa gtcagagcag ctgtgagtta gtcccggggc ttgggctgga tttgagcagg    5280
cagtggggcc tgcagctgca gagggtggac cagcctgacc ctaggagcca gaggtcatcg    5340
tgagggttac agcaaagggc atgggagcag gaattccctg cagaagccct ggccccctta    5400
atggagcgaa gaagccagcg ggaagggaag gtaaatacttg tctaaagttt ctactttgta   5460
cctgagcaat gcctatgaaa cttttaagat atttagtgtg tggaaaataa aactctggag    5520
aagagatcac cacactccag acccactaca tccagaaact ggaagaagat cataaagagc    5580
aggtaccaac caggggccag agcagaaggg aagagggtgg gagaatggct gcgttgagtc    5640
```

-continued

| | | | | | |
|---|---|---|---|---|---|
| aagcaggcga | tttggagggg | tttgtttagt | tttacatttg | cttttctct | acagttggtc | 5700 |
| caaaagctgc | aattcccaga | gactatcctt | aaattgcaat | caggacatgt | tattcaaaac | 5760 |
| agtaagactg | attacacatt | gattacatac | ttgcaaaaat | aaataataaa | ataaacaagg | 5820 |
| atggcagtgt | aggcttctac | tcccctcccc | caataccagt | gaaatccccc | cctttatttt | 5880 |
| ccagtttcat | ttcttttccat | aaattctgtt | atgatgtcat | ttctctctct | ctctctcttt | 5940 |
| ttaaaaaata | taaatccaga | ggagtgactg | aaaatctctg | tgaggaggag | aggttatatt | 6000 |
| cccaccttgg | ccactatgct | gttggtttag | agcacctaac | caggttagtt | agttagtgcc | 6060 |
| tggccactca | gcttagctca | gtcctagtgt | ctctccagga | attgtctggg | tattggccaa | 6120 |
| ataatgttaa | agctggaagg | aacccatagc | catcatcaca | gtcaaggtcc | tagttttaga | 6180 |
| atgaggatac | tgaggccctg | agtgggaagt | cacttgccca | agatgtggca | gcagggttag | 6240 |
| agacagacaa | ggggctggga | ctcagctctt | tcccgcaggg | gctccagcac | tgcattcagc | 6300 |
| cattcctggc | tttctcgcta | gtcactgggg | ctcatgcctg | gacctgggct | aacctgcagt | 6360 |
| aaggcctttg | gcaaacactg | ccagatgcta | tcactccatg | acataagaac | ccataatctg | 6420 |
| aaggcactct | gttttagggg | cagtaggaaa | aggagtgaag | cggccccaaa | gtggagaggg | 6480 |
| ccacactctc | ttattttcac | actcacttct | gtccctttt | ctacacagtc | ttgcatacaa | 6540 |
| gcctggctta | ggctagtggt | ttggtcagag | aaagaggacc | aagagggtgt | gaaggagggg | 6600 |
| tgttcacccc | agctttcagg | tccatgcgcc | aaacctcatt | ttctacatga | caggaagctc | 6660 |
| tcctgatgtg | gagaggcagg | caggcctggc | tgcctctgag | ctgtgcagcg | gcctgtagtc | 6720 |
| ttgaagaaca | tggtgcagaa | gtggcccgct | tccaacagca | cagtcctcac | gtggtgccaa | 6780 |
| cagaaagcag | agatcgagag | agggtgtggt | tggatggggt | gagtgcagta | actaggaagt | 6840 |
| tctgcatccg | aaggagagaa | ggaaaaccat | ataccaccaa | agctgataag | gaagagagca | 6900 |
| tgagggcccc | ctggctttct | ttcataggca | gatgtgtctc | agatctttca | gcaggagagg | 6960 |
| agagatgtgc | ttccagaggg | cagctgggga | cttctggttg | tgctgcagga | agtgctgaga | 7020 |
| cccattctaa | tacatcctgg | aggccgtggc | agctcctcct | tctgggatgc | ttaggaagga | 7080 |
| ggcagataag | ataggcccct | ttttccggta | agtcagacct | gccaggtgaa | ctataggaac | 7140 |
| attttaaacg | aactcagtta | tctcatgttt | gatccctcaa | cctaaaccat | caggcccctt | 7200 |
| tccctggcct | aaaataaggt | cccactgaat | ctgcactcag | agccaggcct | cagatgacct | 7260 |
| ctgctgattc | tctgagttgt | ttaatgtggg | ttccagttat | cccgaactgg | gactgcgaca | 7320 |
| cccctctgtc | acctcagcca | ggatgactct | tcttccagat | catttagaac | agcacttcca | 7380 |
| attgaaacat | aatacaagcc | atatttgtca | ttttttaattt | tctggtagcc | acatctttt | 7440 |
| taaaaggta | aaaaaaacag | ggaaattaat | tgtaataata | cattttaact | gaatatatcc | 7500 |
| aaaatatcct | ttcaccacac | gctcaaaata | aacaattat | aatgagatat | tttacattct | 7560 |
| ttccttcata | tttagccttt | gaaatccggt | gttttttaca | cttacagctc | atctcaattc | 7620 |
| agacactaaa | ttttcattgg | aaatacttga | tctgtattta | gatttcataa | aatttacagt | 7680 |
| tgaaaagca | gagtcacata | cctgaggcat | tccaaacata | ctttaaaatc | tttccaataa | 7740 |
| ctgagttgag | tatctgtttt | taaatttaaa | ctaattaaaa | ttaaataaat | attaaataaa | 7800 |
| ttttaaaatg | tggttcctca | gttccccggg | ccacatttca | gatgttccgt | atgtatctgc | 7860 |
| acatggttaa | tggctaccag | caaacccctc | tctcacctga | gaaggcaact | gctgtcccca | 7920 |
| ctctttcctt | ttgctcccaa | agactcaaaa | aaggggagtc | tcagctttcg | ttgacagaca | 7980 |
| gggctccctt | gtttggtccc | tagcagagcc | tgggcacctt | cttcggggcc | tcaggagaga | 8040 |

```
agcgtaaacc ctacttcctc cctgccgccc ccttctggtc atgcagaact tggggggat    8100 gtggctgtgg ctgcaatgt tctgaactgg ctgtgatggg tcatgatggg aaagtggcca    8160
ggagaaaagc tgcccagtgc ttcctccaga ggctgctccc cacctatccc cccaccatta    8220
ccttctcatt tggggaatgt atgaggaaca gacagacact tctactaagc atgctccccc    8280
ttccccaact ccaaaagaag cttggctgga gattctcagc cagggacttg tgcatcagtg    8340
tgtatttcct atgtgtacag ttatcgccag ctgcttccca gggaccaaga aatgtgaacc    8400
agagtcacaa ccccaaatcc tagtttggca tcagaaaaca acaaggagcc tctctttacc    8460
tctggtccct ggacagtggg gcagatgtaa gggggacctc agccccttac tctgtgaggt    8520
gtcaccttcc cacctgtggc atctacactg tggagggcgg tgggccccct tttctctata    8580
tatcttcagg gaaggaggct aagtgcccct aacgcagcat gaaggaatgg ggttaggcag    8640
aggaaggact cccaggggga gctctctaag tggagacggg tccggagagc acctgtgcca    8700
agtcctcacc tggtgttggc aacagaccc ccagagacaa aggtcgagcc aacactttct    8760
ggcagacctt cctgcagtcc aaggagcctc agatcttgtg gtctacaagt aggcgtctgt    8820
caaccaggtg tcacagcaac caaattttta gttgatgatt cgaactaggg aggtggtagg    8880
aaacagcact acaaaggcag agacctgttc tgagagtgaa ttagcatgca tcaccctgat    8940
taatcctcag aatataatgg agaaggggcc attgccatcc tccccataac acaggtgaga    9000
aaactgaatt ggaagagga agaagaaagt aaggtctttg ggaggctgag gtgggtggat    9060
cacgagctca agagatcaag accatcctgg gcgtggtgct gcatgccttt agtcccagct    9120
actcaagagg ctgaggcagg agaatcattt gaacctggga ggagagggtt gcagtgagcc    9180
aagatcatgc cactgcactc cagcctggcg acagagtgag actccgtctc aaaaaaaaaa    9240 aaaaaaaag aaaggtcaaa gtaaatctgt accaaggttt gtttatttat ttattttag    9300 aaacaaggtc tcactctgtc acccaggctg gagtgcagtg cacaatcat ggctcactgc    9360 agcctccaac tcctgggttc aagccatcct cccttctcag actccccatt gctaggacta    9420
taggtgcaca ctgccacgcc cggctaatat ttcattttat gtagagatgg ggtcttgctg    9480
tgttgccaaa gctgcatcaa ggtttactga gctattgtca acagcttcat cttcctccca    9540
gaaaggacag ctgaaggttt agggtggcac agtttgctgt acctattcag tagtggagct    9600
gggatttgaa cccaggtggt ctggttcctg attctgaatg ttatccact atactacatg    9660 gtgtctgtat ttctctggta aggatagaga tatattccca gcttggccag cttttgctgtt    9720 ggtttagagt acctaaccat gctatttctc ccggcctaaa atgggtgtagg ggggctcagc    9780 tgggtacacc tatagccctc atcatccagt cagtagttct ctaagtctgc tcaactcccc    9840
tccggggtct tcctcctggc tttcctccat tcttacagct gcttttttagg atgacagctt    9900 tgggttttt tttttctta aaaggttagt gctcatttcc tcctcagccc ataattcagg    9960
ttaaaaagaa cccggaacat gcatgcctat ttctgacgat caagtaaaaa caaaacaaa    10020 caaacaaaaa acaaaaacaa aaaaaatgt cttctgagag agactggcgc caggcagctg    10080
ctggtcagag atgggatggg taggaaaaga aatgatgttg ccacttccct ggaagtgtcc    10140
acagcacctt cccctgcca caaccactgt ggcctttctc cttctgcaaa tgcacacaca    10200
caagcgcaga aaagccattt gacatccaca gctgggaaac agacttcaag agactgagac    10260
atgtcttaca ttttttcaaa cagtgaacag ccaatccctc atgcttccac cagccttgtg    10320
ttgtagggag gggctggtgg ctgcaagttg gctagggacc taggggttggc aagggaggag    10380
```

```
ggggactgca gaacattcta gactgggcct cagtattttc atccataccc aggcacaagt      10440
cagtgccgtc aggccagcac tgaccaggac tttctgcaat gatggaagcg ttgcaggtct      10500
gcaatgtcca tatgtggcca cgaagtcctt gaaatatggc tagagtgact gaggagctga      10560 attttttcatt ttatttaata tttatttaaa tagccacatt ggctagtggc taccatatta    10620
aatatatact tttttttttt tttttgtcac actattgccc agggggaat gtagtggcac        10680 gatcttggct cactgcaacc tccgcctccc aggttcaagt gattctcctg cctcagcttc      10740
ccgagcagct gggattacag gcacacacca ccatgcctgg ctgatttttt attttttagta   10800 gagacagggt tttaccatgt tggccaggct ggtctcgaac tcctgacctt gtgatccaac      10860
ctccttggcc tcccaaagtg ctgggattac aggcgtgagc caccatgcct ggcctaagta    10920
gtacattaat atatagtagc cttaggccaa agagaagccc agtgaatcca ggagcacccc      10980
tgctgtttct cacacccatg acgctcatct gtctgcttcc ctgtgccctg cggcagggtt     11040
atcttgctcc agggcaggag catggatgag ataacctccc aaggcatgca ctgggctcta    11100
agccccagct tatattacag aaatacttcc agacctactt ctctttgcct cttgggcaga    11160
tttacacatc tctccattta aaggttattt attgaatact atatgctggt gagacaaaga     11220
gaaatgacaa agctctgccc gtaagaagtt ggctgtttaa attccacagg ggggactaga    11280
atgaaaccca gaacaaattc agctccctttt ttcattcttt gtagagagat tctaggcgtc    11340
ctcatcttat cttctgtcta gaaaggaga tgggagaatc tccccaggtc tgggtggcct     11400
ggcaaagccc gacactcttc ctggactgtg aatttcaagg atgcctctgt ttcttcgatt      11460
tttgtaagct aaggcacaat atctgggtca cctagttttc tcttacaatt gattattagg      11520
tcaagtgaga tagagtgata aactaacacc agcccaggaa caggctgtta atagcaccgg    11580
ggtgtggcta agaggtccgg gggcggggggg tttagatttt aggcaggcag gtctcctgga    11640
tccatccatt gctgtgacca gcaagcaagg tggagtcaga acccttcaga ctctactgga     11700
agagaacagc cgtggcaaaa gggcaggttt ggagaaagtg gttgagcttg gcagggtac     11760 atgcgttgtg caattgtgca gcatggagta tttctcaccc taagatgcct ctgggtctgt    11820
agcagctggg cttgcatcat gacactctct gtgtttgcca ggacatagag gatggtgcaa   11880
tcctcaaaca cgtgttcatg ttaccatggg gagaggctga tgtactgtgt gtgcctctgt      11940
ggatgctgct gcactggggt gtatgggaa ctccttatga atgaaagagg actgagttgg      12000
ccacccaaat gtggcagggg ccagaggcat tggagagcca gtgggaagga ctggaggtat   12060
tatatagaag ccagagattt agatcccacc ccaaaggtaa atactgtatc cagataatat     12120
tatcatcatc ccctcccttta gtcattgaat agggttatga aggtaaggtc tggcctccat      12180
agatcccagc aggagaaatg gatgctgagc attccacatt tcccatcctc tgcaaaaacc    12240
tctcagaaca gcatctcatg ggcggggaag tctggaatat gtctctcttc cttcctggat      12300
cattttccag ttggaggtta cagaaacagc agaatgccat gcacaaacaa gccctgttcc    12360
cctctccctc acctgccttc actctcccac acatgggttc tctccgggcc tcgcttgttt     12420
gtctccctga ctctttaaat atatcctgca gacacacaaa cagaaggaag ggatttatt      12480 gaatgattat tgcagaagta ggagagggag gcacccaaat tccagattta ttttttcttt     12540
gagacagggt ctcactctgt cccccaggct agagtgcagt ggagctatca aagtggagca    12600
atcatggctc acctcagcct cagcctcaac ctccaatctc caacctccta cctccaacct   12660
cccaccttcc gggctcaagc aatcctccgg tctcagcctc ctgagtttct cagactgagg   12720
gcgcacgcct ctatgcccag ctaattttttg tgttttttttt gtagagacgg ggtttcacta   12780
```

-continued

```
tgttgtccag gctggtctcg aactcctggg ctcaggcaat ccactcacct tggcctccca      12840
aagtgctggg attagagata tgagccaccg ctctcaattc caaattccag attttaaaaa      12900
cacttccagg ccgggcttgg tggctcacgc ctgtaatccc agctctttgg gaggccaagg      12960
cgggcggatc acgaggtcag gagatcgaga ccatcctggc taacacggtg aaacccatc       13020 tctactaaaa atacaaaaaa ttagccgggc atggtggcgg cgcctgtag tcccagctac       13080 tcgggaggat gaggcaggag aatggcgtaa acccaggagg cggagcttac agtgagccga      13140
gatcgcgcca ctgcactcca gcctgggcga cagaaggaga ctctgtctca aaaaaaaaa       13200 acaaaaaacg cttccagtcc ctagaagtgt gcccatgctg tgtgggtgtc agtctcccac      13260
gccctctgct ggccacatgg agatattgac ctgtttgtca acaggttccc agagcagact      13320
gttgagttct tttgctgttc acgtgcagaa caatcttcac caggaagtcc tcccgggtat      13380
cctgcctaga tcccttctgc aacctcagtt cattttctct tgatgaaata gctccagagt      13440
agccagtcta cttgttcctt cttgttttat ctaaaacgca aagccttcca caattgaaag      13500
cctatttatg actcagccac agagcagctg agtcgggctg gctgcttctg gcactcagct      13560
ccagtcttac tttccagccc tttaatctcc atggctctgc cctggctccc ctccaagttt      13620
ccgctgtctc tctggagcct acaggtgacc acaagaccct gattagtatc ttcgacactg      13680
gactctgctg ctgcctaagg aataggtccc atggggttaa gtggcaccag aaaccaggag      13740
gcacatcaaa atgttaagcc tgctcttcag aagcagccaa aaagcttgca aagctgggga      13800
aggtgtgccc tcaggagact tgccttgggg aggctgggaa aaggagagag tttgcaaaag      13860
cattttgagt tccttaaatg aagagagata caagaatcta cattttgtat gccagtatca      13920
tggttgcttg gccccgggc agtacttgaa cactttcaaa gaaaagagta agagaggtca       13980
aaataaattt accccaaggt ttatcaaacc gttgtcaaca gccccatccc cctcccagaa      14040
agggtgactc aaggttaagg acagcccaca gcacttctta gaaaaagtcc caaaggtga      14100 aaggtcttga gaagagctgt tgagggaagg ctgtgggcca ccatgcttct gtgtcccca      14160 aggccaaaga gagaataagc taaaatgaca gctggaaaag ggcaccctct gaccaaatgg      14220
acagagcctc ccccaacagg tagccagagg aggatggaat ggcacccca tttcagatgt       14280 ccttaagaac tagagagata gatgcttatt tctgcttgga cacaggggga tggactaaat      14340
ggcctacgga aaggattcca ggaactgcta caccagccac aggagagaag ccagcttccc      14400
aggctgtctc cccttgaaga ggtgacaatg tgttggctct ccaggccagg ctggggcagc      14460
ccactgaagg agacgcatag acgcatgcgc tggtcagcag ccagcccact cccccacctg      14520
ccctcacttt atccagttac aatcttgatt gaggaagggg tccaggcttc tccaatctga      14580
accccctcca ggctttcagt agccaccata tcctgtctgc cctcccccct acagtagtca      14640
actacttttt gaggattaaa atgcgtggtg atgctgaggt tgagtggcac ggctccagtc      14700
cctccataag acgtgcccaa aagcccttct gtgcaatggt tagcactccc tctccctact      14760
ccctcttctc caagatctga gccttggcgt gaggcctgtg ttactagata acggagcccc      14820
agcctttcaa tttgtacaaa gtccccaaac cagccatgct tctcccttcc tcctgccaat      14880
ctcacttgcg ctacaaccaa gaaaagtcaa tttaccccag aacatgaccc ttttaactaa      14940
tccctagaat cctgcattcc acctaccaga gatgtcaccc tattgatgag tcgtcacagc      15000
agggtctgat agagcagaat cgaggtactg ggacatcaag acatgactgg gaagaggggg      15060
tgagagtcca gaagggtac caggattctc aggttgaatt ttatttaggg agagcccacc       15120
```

```
caccaccttg ctatttgctt tccccaagtc atcatcttcc tctccagtaa ttacgtccct   15180
tcctttcctg tgaataaata cccaaagcaa ctcaccacca ggaacgctgc gaacctttgg   15240
aggcttcttt agggcaggga ccttctctgc caaggcctta agaccagat acctatttca    15300 ttagacttga caaatcctga gccaagagag aaacagatgc ttgggtgctt cctgccacct   15360
gccatcctgc ccaggttagg ccaggtgtcc aaatgccttt cctaactcac acctggaact   15420
tgcccagggc tgcaagctca gaagtcaggt tctatacctg cccagaggca taaaacagcg   15480
tcttctcaaa aaagcttctc tttccttgca ccccacccc acttcctgga attctaccca    15540
cttcttctgt tccccatccc agatgtctgg cggtcactgt tcctggacat cccagtgatc   15600
atggagtaga tggagaacag aattttcttt cacctcattt cagttattta aggtcactca   15660
aagctctatt ttctctttcc agtatttgaa aaagaggga ggcaatgaag cagggcccc    15720 ccacctccac tcacccctgc atctggtccc actgtgaggc atcctggcca cacgctgccc   15780
gcctggaaac aacaatctaa agttccccca ttctggttcc tctgaggctg ggggaggtca   15840
aggatctgag aggagaaggg gacccaggga tggatgccta tgagatcaga atttagggga   15900
aaactgcgca ccaagaaaag gccggacggg tggaattaag gatcaacaaa tacatcaaca   15960
aagtctgact tctctaaagg tcaaaagcca gctaagtata gactgtcagc aagccactcc   16020
tatatataac tgtcccggtc tcagccagct gtcggcctct ctcagtccag agctgagtaa   16080
cgtcccagcc tcccaggccc ccgagcaccg cgccagttct gagccagagc aggagcaagg   16140
cctccgactt ccacttggcc ccacgccggt cccctccggg cctacatttc tggctctccc   16200
ctcccctcct cctgccgctt atgaaggtcc tcaccaccct gctgctccag accccaggac   16260
cccctcctcc taggttcccc aggtccaaag agacctcaac atccagcagc tctgaaagtg   16320
caaagatctc actaacagga cagccttttgc ccttctcgtc cacgccctga ctgtgtcatc   16380
tgcctccatg ggcccagatt cccggggttcc tacttctcag ccccacctcc agccatgtcc   16440
catctacttg gccatccccc agcaagcaaa ccgctcgctg ccaccttcat ccttgcagag   16500
gccattttcc ttgcccttcc tccttactgc ccccagaagg cctgctccgt cctcacccat   16560
cagtctgtca gtctctcgat tctcctcctc tgtgaagcct ccctgcctgc actctctgct   16620
tgactccaag catgccagaa acttcctgcc acttaaatga gcattccctc tgcttcctgg   16680
ttcttatccc cctgctttca gggtgtgctc caggagggca gagacacatc tgcttcagcc   16740
tttattactc ccctcacccc aaactgccca gccctgggct ctggccgtgt gcaccttggc   16800
ccacgggggc tgaccctccg gctccttctc ctgcagagag agactcccgt gagcacgagg   16860
agcccaccac ctctgagatg gccgaggaga cctactcccc caagatcttc cggcccaaac   16920 acaccgcat ctccgagctg aaggctgaag cagtgaagaa ggaccgcaga aagaagctga   16980
cccagtccaa gtttgtcggg ggagccgaga acactgccca ccccggatc atctctgcac   17040 ctgagatgag acaggagtct gagcaggtgc atctcgggga ttccctcatt ccctcccagc   17100
ttttgacctt ttcctgcatc taaatggaca ttcatggcgg caggaggtgc tagactagac   17160
ccagcagagg acctacagcc caccatgtgg ctcagcttag gacgtgggag tagagtttcc   17220
agagcataca cttgtcaggg ccaagggctt gtgcaagtaa gtgggaatag aggcggtgct   17280
catttgagga gagtgtgtgc cagcccagcg gccacgtacc aggtacctgg gccctgcagc   17340
tgtgtccagt ccaaggcaga gactgaatat tctcctagag catctagaaa tgggcacctc   17400
tggacattgt tactcagcag aagagaaaag ctgcagggga ggggtggac tggaacacaa    17460 aagagaaagt atgactccgt acctggccaa aggcaggctt tgtatgatcc cagcgcacgt   17520
```

```
gacaggtgac agggaggaaa gatctttggt agcagatgat tagaaccaaa ggtggtgact   17580
ttcctccaga gacccttcag cccccacccc ctgggccatt cgtcagcgca gctgggtggt   17640
tttcccttgg tctcgccacg cctctcaccc tcctgtccac acaggcccc tgccgcagac    17700 acatggaggc ttccctgcag gagctcaaag ccagcccacg catggtgccc cgtgctgtgt   17760
acctgcccaa ttgtgaccgc aaaggattct acaagagaaa gcaggtacgt cccctgccct   17820
gagctccagg ctcagactgc tccaaaaatg gcacctgcca ggaaactcca ccttgggcaa   17880
gtgcctaagg tttccaccgt taaccactta gtgtttcctg ggcctcagat acccattcat   17940
ataccacgat catgactttc cacattccct actatgctgt aatccatttc ctcattctct   18000
cctatgcggt aatccactat gctttccaca gtcgcctta gctacatgaa ttccttgcaa    18060
aaggtaactc tgtaacacta tcgcacagca cgtatcattg gtgcaccgca cactcaggaa   18120
tttaaaccat attttctctg tgaaccacct gaaatcagtt catgtccctt cacagccagg   18180
ctctcctttg ggcaatggtt cttagatttc caagggcatc ctatccctgg agggcatggc   18240
tgatggctgg gccccacccc tgcagtttct gattggtaga cctggggtgg actccggggt   18300
ggacacgtga ccctgatgct gctttaaggg caccaataat ctaaatgtaa gagccaggcc   18360
acactggggc aaatcttggc tctgccactt actagctgtg tcctgttact caccatttaa   18420
tgtctctgtg cctccagacc cttgtgtaaa atggtgaatg aggagtgagt gattggtctt   18480
tgtaaagcac ttagaacagt acctactgcc taccaaacgt tgagtggtgt ctactacatg   18540
ataacaccac aaatcatgcc tccttctgtt attattatta ccatcatcat tattattgga   18600
tcataactct cttgagaatc cctgcagagt ttcacgttgg gggaactcaa atgggtaata   18660
tttaaaacgg gactataagc caggcacagt ggctcacgcc tgtaatccca gctactccag   18720
aggctgaggc aggaagatca cttgggctca ggagttttag accaacctgg gcaacataac   18780
gggaccccat gtctgaaaaa aaaaaaagga agaaaggga ttgaaggagc ttgccaaggg    18840
taggctgcct aaattcacat tttccctggg tctttccgtg aaatggggac accagaaacc   18900
caagggtcgg gtctagtgcc ctcaactctc tggggatgag agtcttgcct tggggtagac   18960
aagaggcagg gcagggagga gcagagccct ggggtgcggc cgtcctcacc gcctgttgct   19020
ctactcaccc cagtgcaaac cttcccgtgg ccgcaaacgt ggcatctgct ggtgcgtgga   19080
caagtacggg atgaagctgc caggcatgga gtacgttgac ggggactttc agtgccacac   19140
cttcgacagc agcaacgttg agtgatgcgt ccccccccaa cctttccctc acccctccc    19200 acccccagcc ccgactccag ccagcgcctc cctccacccc aggacgccac tcatttcatc   19260
tcatttaagg gaaaaatata tatctatcta tttgaggaaa ctgaggacct cggaatctct   19320
agcaagggct caacttcgaa aatggcaaca acagagatgc aaaaagctaa aagacaccc    19380 ccccccttta aatggttttc tttttgaggc aagttggatg aacagagaag ggaagagagg   19440
aagaacgaga ggaagagaag ggaaggaagt gtttgtgtag aagagagaga aagacgaata   19500
gagttaggaa aaggaagaca agcaggtggg caggaaggac atgcaccgag accaggcagg   19560
ggcccaactt tcacgtccag ccctggcctg gggtcgggag aggtgggcgc tagaagatgc   19620
agcccaggat gtgcaatca atgacactat tggggttcc caggatggat tggtcagggg     19680
gagaaaggaa aaggcaaaac actccaggac ctctcccgga tctgtctcct cctctagcca   19740
gcagtatgga cagctggacc cctgaacttc ctctcctctt acctgggcag agtgttgtct   19800
ctccccaaat ttataaaaac taaaatgcat tccattcctc tgaaagcaaa acaaattcat   19860
```

-continued

```
aattgagtga tattaaatag agaggttttc ggaagcagat ctgtgaatat gaaatacatg      19920
tgcatatttc attccccagg cagacatttt ttagaaatca atacatgccc caatattgga      19980
aagacttgtt cttccacggt gactacagta catgctgaag cgtgccgttt cagccctcat      20040
ttaattcaat ttgtaagtag cgcagcagcc tctgtggggg aggataggct gaaaaaaaaa      20100
agtgggctcg tatttatcta caggactcca tatagtcata tataggcata taaatctatt      20160
cttttttctt gtttttttct ttcttcctttc ctttcaaagg tttgcattaa cttttcaaag     20220
tagttcctat aggggcattg aggagcttcc tcattctggg aaaactgaga aaacccatat      20280
tctcctaata caacccgtaa tagcattttt gcctgcctcg aggcagagtt tcccgtgagc      20340
aataaactca gcttttttgt ggggcacagt actggatttg acagtgattc cccacgtgtg      20400
ttcatctgca cccaccgagc caggcagagg ccagccctcc gtggtgcaca cagcacgcgc      20460
ctcagtccat cccattttag tctttaaacc ctcaggaagt cacagtctcc ggacaccaca      20520
ccacatgagc ccaacaggtc cacgatggat ccaccagtcc caccccagcc ttttcctttc     20580
atctgaacag aatgtgcatt tttggaagcc tccctcactc tccatgctgg cagagcagga     20640
gggagactga agtaagagat ggcagaggga gatggtggca aaaggttta gatgcaggag      20700 aacagtaaga tggatggttc cggccagagt cgatgtgggg aggaacagag ggctgaaggg    20760
agagggggct gactgttcca ttctagcttt ggcacaaagc agcagaaagg gggaaaagcc    20820
aatagaaatt ccttagcttt ccccaccata tgtattttct aggatttgag aggaaagaga    20880
ggaaaatggg ggaatgggtt gcaaaataga aatgagctta atccaggccg cagagccagg    20940
gaaggtgagt aactttagga gggtgctaga ctttagaagc cagataggaa gaatcagtct    21000
```

<210> SEQ ID NO 12
<211> LENGTH: 374
<212> TYPE: DNA
<213> ORGANISM: Homo sapiens
<220> FEATURE:

<400> SEQUENCE: 12

```
gttgtctctc cccaaattta taaaaactaa atgcattcc attcctctga aagcaaaaca       60
aattcataat tgagtgatat taaatagaga ggttttcgga agcagatctg tgaatatgaa     120
atacatgtgc atatttcatt ccccaggcag acatttttta gaaatcaata catgccccaa     180
tattggaaag acttgttctt ccacggtgac tacagtacat gctgaagcgt gccgtttcag     240 ccctcatttta attcaatttg taagtagcgc agcagcctct gtggggagg ataggctgaa      300 aaaaaaagt gggctcgtat ttatctacag gactccatat agtcatatat aggcatataa      360
atctaaaaaa aaaa                                                       374
```

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13

```
gagcaacacc atcttctctt                                                  20
```

<210> SEQ ID NO 14
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 14
taggcggcca gcagcaggag                                              20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
gcgtgcagcg gcttctcctc                                              20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
cagcagggcg tgcagcggct                                              20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
ttcgttgagg caaaccccgc                                              20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
ctcttttcgt tgaggcaaac                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gtagctcttt tcgttgaggc                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
tttctgcggt ccttcttcac                                              20

```
<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
agcttctttc tgcggtcctt                                            20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
actgggtcag cttctttctg                                            20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
aacttggact gggtcagctt                                            20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
cctgtctcat ctcaggtgca                                            20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
catgcgtggg ctggctttga                                            20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ggcaccatgc gtgggctggc                                            20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 27
tgggcaggta cacagcacgg                                                    20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tagaatcctt tgcggtcaca                                                    20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
tcttgtagaa tcctttgcgg                                                    20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gctttctctt gtagaatcct                                                    20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gtcctcagtt tcctcaaata                                                    20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ccgaggtcct cagtttcctc                                                    20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
agattccgag gtcctcagtt                                                    20

<210> SEQ ID NO 34
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 34
gctagagatt ccgaggtcct                                           20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cccttgctag agattccgag                                           20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
cctaactcta ttcgtctttc                                           20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
ggagaggtcc tggagtgttt                                           20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gatctgcttc cgaaaacctc                                           20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ctttgcagct ctttcctagc                                           20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
```

-continued

```
cttgcaaaaa tgtagagaga                                          20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gctttggctg cctgccacct                                          20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ctgcaggaga aggagccgga                                          20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
actgtagtca ccgtggaaga                                          20
```